United States Patent [19]

Davidson, III et al.

[11] Patent Number: 4,940,822
[45] Date of Patent: Jul. 10, 1990

[54] SUBSTITUTED BENZENEMETHANOL COMPOUNDS, INTERMEDIATES THEREOF, AND PREPARATION THEREOF

[75] Inventors: James G. Davidson, III; Brian S. Swierenga, both of Holland, Mich.

[73] Assignee: Warner-Lambert Company, Ann Arbor, Mich.

[21] Appl. No.: 267,428

[22] Filed: Nov. 4, 1988

[51] Int. Cl.$^5$ .............................................. C07C 33/46
[52] U.S. Cl. .................................... 568/812; 568/705; 568/634; 568/640; 568/655; 568/807; 568/808; 568/809
[58] Field of Search ............... 568/812, 807, 808, 809, 568/650, 634, 655, 640, 705

[56] References Cited

U.S. PATENT DOCUMENTS

| | | | |
|---|---|---|---|
| 4,105,703 | 8/1978 | Motta | 260/665 |
| 4,772,615 | 9/1988 | Pavia | 514/318 |

OTHER PUBLICATIONS

"Synthesis of N-Acetyl-S-Trifluoromethylphenyl-d-l-Cysteine Esters", Ondrus et al., Aust. J. Chem., 1979, 32, 2313–6.
"Continuous Reactor Model for the Use of Butyl Lithium in the Pilot Plant", Goel, Chemistry and Industry, Aug. 17, 1974, pp. 665–666.
"Sleep-Inducing N—Alkyl-5-[M-(Trifluoromethyl)-Phenyl]-5-Hydroxy-2-Pyrrolidinones and N-Alkyl-3-(Trifluoromethyl)Cinnamamides", Houlihan et al., Journal Medical Chemistry, 1985, 28, 28-31.
"Synthesis and Antimalaria Activity of Benzotrifluoride Derivatives", Novotny et al., Journal Pharmaceutical Science, vol. 62, No. 6, Jun. 1973, pp. 910–913.
Bretherick, L., Chem. and Ind., 1971, p. 1017, and attached paper, "Use Caution in Preparing-Trifluoromethylphenylmagnesium and Trifluoromethylphenyllithium".
Handbook of Reactive Chemical Hazards, L. Bretherick, 1979, pp. 137, 616, 617.
"Polyhalogenated α-Oxides III Polyfluorinated α-Oxides Containing the Trifluoromethyl Group", Bekker et al., 1974, pp. 1663–1666.
"Carbonation of Ortho-Meta- And Paratrifluoromethylphenyllithium Compounds", Soloski et al., Journal of Organometallic Chemistry, 157 (1978), 373–377.

*Primary Examiner*—Werren B. Lone
*Attorney, Agent, or Firm*—Pollock, Vande Sande & Priddy

[57] ABSTRACT

Compounds of the formula:

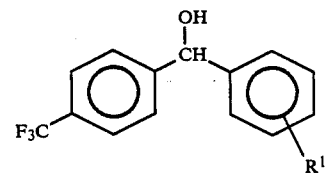

wherein R$^1$ is hydrogen, halo, halo-substituted alkyl, alkyl, cycloalkyl, aralkyl, aryl, heterocyclic, alkoxy, alkaryl, aryloxy; thioalkoxy, nitro, or N,N-dialkylamino are prepared by reacting 1-bromo-4-(trifluoromethyl)-benzene with n-butyl lithium; reacting the product with a benzaldehyde of the formula:

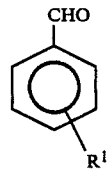

to produce a novel intermediate such as lithium 4-(trifluoromethyl)-α-]4-(trifluoromethyl)phenyl]benzenemethanol, and then reacting the lithium product with an acid or acid salt.

34 Claims, No Drawings

SUBSTITUTED BENZENEMETHANOL COMPOUNDS, INTERMEDIATES THEREOF, AND PREPARATION THEREOF

TECHNICAL FIELD

The present invention is concerned with an efficient and relatively safe process for the preparation of substituted benzenemethanol compounds such as 4,4'-bis(trifluoromethyl)benzhydrol and to the preparation of the intermediates thereof. Substituted benzenemethanol compounds, and especially 4,4'-bis(trifluoromethyl) benzhydrol, are suitable for preparing such pharmaceutical compounds as anticonvulsants disclosed in U.S. Pat. No. 4,772,615, disclosure of which is incorporated herein by reference.

The present invention is also concerned with the novel lithium alkoxide intermediates such as lithium 4-[trifluoromethyl]-α-[4-(trifluoromethyl)phenyl]benzenemethanol.

BACKGROUND ART

In the preparation of certain anticonvulsants disclosed in U.S. Pat. No. 4,772,615, such as 1-[2-[bis[4-(trifluoromethyl)phenyl]methoxy]ethyl]-3-pyridine carboxylic acid, it is necessary to prepare as an intermediate, p-trifluoromethyl phenyl lithium. This compound has been prepared by metallation of p-bromobenzotrifluoride with n-butyl lithium in diethyl ether. However, this reaction must be carefully carried out in view of the explosive instability reported for p-trifluoromethylphenyllithium. In addition, the yields of the desired compound employing that reaction were rather modest and not satisfactory from a commercial standpoint. Moreover, this reaction was not especially suitable for scale-up to provide commercially desired quantities of material.

SUMMARY OF THE INVENTION

The present invention is concerned with producing substituted benzenemethanol compounds in a safe and efficient manner whereby relatively high yields of product can be obtained. The present invention significantly reduces, if not entirely eliminating, the risk of an explosion.

In particular, the present invention is concerned with a process for the preparation of a compound of the formula:

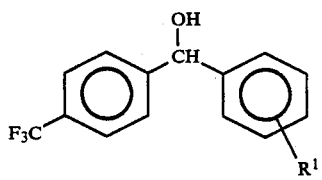

wherein $R^1$ is represented by hydrogen, halo, halo-substituted alkyl groups such as trihalomethyl groups, nitro alkyl groups, aralkyl groups, cycloalkyl groups, aryl groups, alkaryl groups, heterocyclic groups, alkoxy groups, aryloxy groups, thioalkoxy groups, and N,N-dialkylamino groups.

The process includes reacting 1-bromo-4-(trifluoromethyl) benzene with n-butyl lithium in an inert solvent such as an ether solvent.

The product obtained thereby is then reacted with a benzaldehyde of the formula:

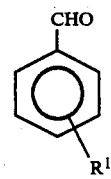

wherein $R^1$ has the same meaning stated above.

The product from this latter step is reacted with an acid or acid salt to thereby produce the desired compounds.

The process of the present invention is advantageously carried out in a continuous manner.

In addition, the present invention is concerned with producing intermediates employed to produce the desired product by continuous process, as well as with the lithium alkoxide intermediates:

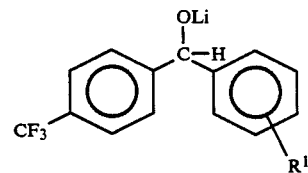

In particular, p-(trifluoromethyl)-phenyllithium is continuously produced by continuously introducing 1-bromo-4-(trifluoromethyl)benzene and n-butyl lithium in the presence of an inert solvent, such as an ether solvent.

In addition, the present invention is concerned with producing an intermediate having the formula:

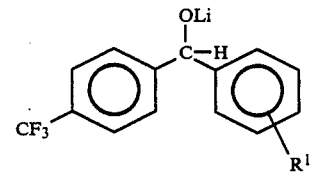

wherein $R^1$ is defined above. This process includes reacting 1-bromo-4-(trifluoromethyl)benzene with n-butyl lithium in an inert solvent.

The product obtained is reacted with a benzaldehyde of the formula:

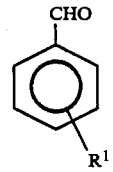

wherein $R^1$ is defined above.

BEST AND VARIOUS MODES FOR CARRYING OUT INVENTION

The first stage or step of the process of the present invention includes reacting 4-trifluoromethylbromobenzene with n-butyl lithium. The reaction is carried out in the presence of inert diluents. For instance, the 4-trifluoromethylbromobenzene is usually employed as a solution in an ether solvent such as diethyl ether, tetrahydrofuran, di-n-butyl ether, dimethoxyethane, methylal, dioxane, and preferably in methyl t-butyl ether and preferably at concentrations of about 0.05 to about 5 molar, typical of which is about 0.67 molar. Mixtures of ether solvents can be employed when desired.

The n-butyl lithium is usually employed as a solution in a saturated aliphatic hydrocarbon solvent, typically, hexane, heptane, cyclohexane, and preferably at concentrations of about 0.1 molar to about 10 molar, preferably about 0.55 to about 5.5 molar, with about 1.6 molar being typical. The n-butyl lithium is usually employed in equimolar amounts or in slight excess of the stoichiometric amount for reacting with the 4-trifluoromethylbromobenzene.

The residence time for this step of the process is usually about 10 seconds to about 100 minutes, preferably about 30 seconds to about 20 minutes, typical of which is about 1 minute. This step of the process is usually carried out at temperatures of about $-10°$ C. to about $0°$ C.

The next step of the process of the present invention involves reacting the lithium product from the first step with a benzaldehyde of the formula:

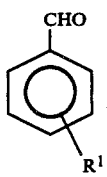

wherein $R^1$ is hydrogen, halo, halo-substituted alkyl groups, nitro, alkyl groups, aralkyl groups, cycloalkyl groups, aryl groups, alkaryl groups, heterocyclic groups, alkoxy groups, aryloxy groups, thioalkoxy groups, and N,N-dialkylamino groups. The $R^1$ group is preferably located at the para position. The preferred $R^1$ substituent being $CF_3$ (trifluoromethyl) and the preferred benzaldehyde being 4-trifluoromethylbenzaldehyde.

The halo-substituted alkyl groups include the trihalomethyl groups and preferably trifluoromethyl.

The alkyl groups usually contain 1-8 carbon atoms and preferably 1-4 carbon atoms and include methyl, ethyl, propyl, isopropyl, n-butyl, sec-butyl, iso-butyl, and tert-butyl.

The cycloalkyl groups usually contain 3-6 carbon atoms and include cyclopentyl and cyclohexyl.

The aryl groups include phenyl and naphthyl.

The alkoxy groups generally contain 1-8 carbon atoms and preferably 1-4 carbon atoms and include methoxy, ethoxy, and propoxy groups.

Examples of aryloxy groups are phenoxy and naphthoxy.

The thioalkoxy groups usually contain 1-8 carbon atoms and preferably 1-4 carbon atoms and include thiomethoxy, thioethoxy, and thiopropoxy.

Examples of suitable halo groups are F, Cl, and Br.

Examples of an alkaryl groups include tolyl and xylyl.

Examples of heterocyclic groups are those containing N, O, and/or S in the ring and include pyridine, morpholine, furan, pyran, and thiophene.

The alkyl moieties of the dialkylamino groups usually contain 1-8 carbon atoms and preferably 1-4 carbon atoms and include methyl and ethyl.

The benzaldehyde is usually employed as a solution in an ether, preferably the same ether as used in the first step and most preferably methyl-t-butyl ether.

The benzaldehyde is preferably used at concentrations of about 0.05 molar to about 5 molar, typically about 0.96 molar. The benzaldehyde is usually employed in excess of the stoichiometric amount for reacting with the lithium product from the first step.

The residence time for this step of the process is usually about 5 seconds to about 100 minutes, preferably about 20 seconds to about 15 minutes, typical of which is about 0.6 minutes. This step of the process, which is extremely exothermic, is usually carried out at about $-10°$ C. to about $0°$ C.

The product produced in this step of the process, the lithium alkoxide of the desired substituted benzenemethanol compound (e.g., 4,4'-bis(trifluoromethyl)benzylhydrol), is then reacted with an aqueous solution of an acid salt, preferably ammonium chloride, or aqueous solution of a mineral acid, such as HCl and $H_2SO_4$, to produce the desired substituted benzenemethanol compound. This step of the reaction is preferably carried out by employing a saturated aqueous solution of the acid salt.

The process is preferably carried out in a continuous manner in a tube reactor or other small residence volume continuous reaction system which minimizes the possibility of explosion. The intermediates are prevented from building up as they are reacted as soon as they are formed.

The following non-limiting examples are presented to further illustrate the present invention.

EXAMPLE 1

A reaction tube of 0.25 in. inside diameter (ID) and 0.375 in. outside diameter (OD) and 15 feet long is supplied through a mixing tee from two 3 foot lengths of 0.125 in. ID and 0.25 in. OD. These smaller feed lines separately carry a 0.67 molar (M) solution of 4-trifluoromethyl bromobenzene in methyl t-butyl ether and a 1.6M solution of n-butyl lithium in hexane at flow rates of about 77 ml/min. and about 55 ml/min., respectively. The solution from this first 15 foot reaction tube flows into a second reaction tube of the same dimensions through a second mixing tee. At this mixing tee another smaller feed line, having the same dimensions as the two feeding the first reaction tube, enters carrying a 0.96M solution of 4-trifluoromethyl benzaldehyde in methyl t-butyl ether at a flow rate of about 35 ml/min. The product solution from the second reaction tube flows into a 50 gallon glass-lined reactor containing a stirred saturated solution of aqueous ammonium chloride. These flow rates yield a residence time of about 1.10 minutes in the first reaction tube and about 0.87 minutes in the second reaction tube. The three reagent solution supply lines are supplied by similar feed tank and delivery systems. Each reagent supply system contains a 10 liter stainless steel vessel with sidearm level gauge, valved bottom outlet, and two top ports. These vessels are refilled on an as-needed basis during the reaction sequence. The top ports are used for nitrogen blanketing and reagent charging. The reagent solution is allowed to flow from the bottom outlet to a magnetically driven gear pump through a 0.25 in. OD tube. The solution is then pumped through another 0.25 in. OD tube through a variable area glass tube flowmeter. The smaller feed lines mentioned above are connected to the other end of these flowmeters. The entire reaction zone from the first mixing tee to the end of the second reaction tube inclusively is immersed in an ethylene glycol/water cooling bath and held at a temperature from about 0° C. to about −10° C.

Upon initial charging of the three supply systems and stabilization of the temperature bath, the reaction is begun by starting the two pumps supplying reagent solution to the first and second feed tubes and after about one minute starting the pump supplying reagent to the third feed tube. The pumps are initially set at the flow rates disclosed above. Periodic samples are drawn and analyzed by gas chromatograph. From the results of those samples, minor adjustments can be made to the pump speeds. GC analyses generally varied from 85% to 95% 4-(trifluoromethyl)-4-(trifluoromethyl)phenyl benzenemethanol. The reaction proceeds continuously until all of the pre-prepared starting materials are consumed (about 12 hours). Following this reaction the waste water layer is removed, the organic/product layer is vacuum distilled to remove the methyl t-butyl ether, and the product 4-(trifluoromethyl)-4-(trifluoromethyl) phenyl benzenemethanol is recrystallized from heptane.

EXAMPLE 2

Example 1 is repeated, except that flow rates of about 91 ml/min, about 51 ml/min, and about 42 ml/min for the three reagent solutions 4-trifluoromethylphenyl bromide in methyl t-butyl ether, n-butyl lithium in hexane, and 4-trifluoromethyl benzaldehyde in methyl t-butyl ether, respectively, are used. These flow rates yield a residence time of about 1.02 minutes in the first reaction tube and 0.79 minutes in the second reaction tube. GC analyses of the crude reaction mixture vary from 80% to 95% 4-(trifluoromethyl)-4-(trifluoromethyl) phenyl benzenemethanol.

EXAMPLE 3

Example 1 is repeated, except that flow rates of about 103 ml/min, about 55 ml/min, and about 40 ml/min for the three reagent solutions 4-trifluoromethylphenyl bromide in methyl t-butyl ether, n-butyl lithium in hexane, and 4-trifluoromethyl benzaldehyde in methyl t-butyl ether, respectively, are used. These flow rates yield a residence time of about 0.92 minutes in the first reaction tube and about 0.73 minutes in the second reaction tube. GC analyses of the crude reaction mixture vary from 80% to 93% 4-(trifluoromethyl)-4-(trifluoromethyl)phenyl benzenemethanol.

EXAMPLE 4

Example 1 is repeated, except that flow rates of about 78 ml/min, about 50 ml/min, and about 42 ml/min for the three reagent solutions 4-trifluoromethylphenyl bromide in methyl t-butyl ether, n-butyl lithium in hexane, and 4-trifluoromethyl benzaldehyde in methyl t-butyl ether, respectively, are used. These flow rates yield a residence time of about 1.13 minutes in the first reaction tube and about 0.85 minutes in the second reaction tube. GC analyses of the crude reaction mixture vary from 90% to 98% 4-(trifluoromethyl)-4-(trifluoromethyl)phenyl benzenemethanol.

EXAMPLE 5

A reaction tube of 0.194 in. inside diameter (ID) and 0.25 in. outside diameter (OD) and 17 feet long is supplied through a mixing tee from two 2.5 foot lengths of 0.085 in. ID and 0.125 in. OD. These smaller feed lines separately carry a 0.67 molar (M) solution of 4-trifluoromethyl bromobenzene in methyl t-butyl ether and a 1.6M solution of n-butyl lithium in hexane at flow rates of about 9.4 ml/min. and about 4.0 ml/min., respectively. The solution from this first 17 foot reaction tube flows into a second reaction tube of the same dimensions through a second mixing tee. At this mixing tee another smaller feed line, having the same dimensions as the two feeding the first reaction tube, enter carrying a 0.96M solution of 4-trifluoromethyl benzaldehyde in methyl t-butyl ether at a flow rate of about 6.7 ml/min. The product solution from the second reaction tube flows into a 20 liter glass vessel containing a stirred saturated solution of aqueous ammonium chloride. These flow rates yield a residence time of about 7.37 minutes in the first reaction tube and about 4.91 minutes in the second reaction tube. The three reagent solution supply lines are supplied by similar feed tank and delivery systems. Each reagent supply system contains a 1 liter glass dropping funnel.

These funnels are refilled on an as-needed basis during the reaction sequence. The top stopcock hole is used for nitrogen blanketing and reagent charging. The reagent solution is allowed to flow from the bottom outlet to a magnetically driven gear pump through a 0.125 in. OD tube. The solution is then pumped through another 0.125 in. OD tube through a variable area glass tube flowmeter. The smaller feed lines mentioned above are connected to the other end of these flowmeters. The entire reaction zone from the first mixing tee to the end of the second reaction tube inclusively is immersed in an ethylene glycol/water cooling bath and held at a temperature from 0° C. to −10° C.

Upon initial charging of the three supply systems and stabilization of the temperature bath, the reaction is begun by starting the two pumps supplying reagent solution to the first and second feed tubes and after about one minute starting the pump supplying reagent to the third feed tube. The pumps are initially set at the flow rates disclosed above. Periodic samples are drawn and analyzed by gas chromatograph. From the results of those samples, minor adjustments can be made to the pump speeds. GC analyses generally varied from 90% to 98% 4-(trifluoromethyl)-4-(trifluoromethyl)phenyl benzenemethanol. The reaction proceeds continuously until all of the pre-prepared starting materials are consumed (about 1 hour). Following this reaction the waste water layer is removed, the organic/product layer is vacuum distilled to remove the methyl t-butyl ether, and the product 4-(trifluoromethyl)-4-(trifluoromethyl) phenyl benzenemethanol is recrystallized from heptane.

EXAMPLE 6

Example 5 is repeated, except that flow rates of about 14.3 ml/min, about 6.0 ml/min, and about 10.0 ml/min for the three reagent solutions 4-trifluoromethylphenyl bromide in methyl t-butyl ether, n-butyl lithium in hexanes, and 4-trifluoromethyl benzaldehyde in methyl t-butyl ether, respectively, are used. These flow rates yield a residence time of about 4.94 minutes in the first reaction tube and about 3.29 minutes in the second reaction tube. GC analyses of the crude reaction mixture vary from 85% to 95% 4-(trifluoromethyl)-4-(trifluoromethyl)phenyl benzenemethanol.

EXAMPLE 7

Example 5 is repeated, except that flow rates of about 28.6 ml/min, about 12.0 ml/min, and about 20.0 ml/min for the three reagent solutions 4-trifluoromethylphenyl bromide in methyl t-butyl ether, n-butyl lithium in hexanes, and 4-trifluoromethyl benzaldehyde in methyl t-butyl ether, respectively, are used. These flow rates yield a residence time of about 2.47 minutes in the first reaction tube and about 1.65 minutes in the second reaction tube. GC analyses of the crude reaction mixture vary from 85% to 95% 4-(trifluoromethyl)-4-(trifluoromethyl)phenyl benzenemethanol.

Having thus described our invention, what we claim as new and desire to secure by Letters Patent is:

1. A compound of the formula:

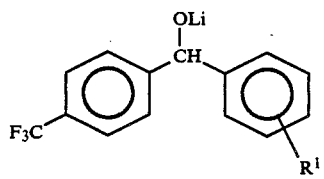

wherein R¹ is selected from the group of hydrogen, halo substituted alkyl group, halo, nitro, alkyl group, aralkyl group, cycloalkyl group, aryl group, alkaryl group, heterocyclic group containing a member selected from the group of N, O, S, or mixtures thereof, alkoxy group, aryloxy group, thioalkoxy group, and N,N'-dialkylamino.

2. The compound of claim 1 wherein R¹ is CF₃.

3. The compound of claim 1 which is lithium 4-(trifluoromethyl)-α-[4-(trifluoromethyl)phenyl]benzenemethanol.

4. A process for preparing the compound of claim 1 which comprises:
   (a) reacting 1-bromo-4-(trifluoromethyl) benzene with n-butyl lithium in an inert solvent, and
   (b) then reacting the product of step a) with a benzaldehyde of the formula

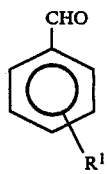

in an inert solvent.

5. The process of claim 4 being carried out continuously.

6. The process of claim 5 wherein a solution of 1-bromo-4-(trifluoromethyl)benzene in an inert solvent and a solution of n-butyl lithium in an inert solvent are introduced simultaneously in a continuous manner in a tube reactor; a solution of p-(trifluoromethyl)phenyllithium is exited to a second tube reactor wherein said benzaldehyde in an inert solvent is introduced in a continuous manner.

7. The process of claim 6 wherein the inert solvent for the n-butyl lithium is a saturated aliphatic hydrocarbon and the inert solvent for the 1-bromo-4-(trifluoromethyl)benzene and for the benzaldehyde is an ether.

8. The process of claim 7 wherein said hydrocarbon is hexane and said ether is methyl-t-butyl ether.

9. The process of claim 7 wherein about 0.05 to about 5 moles of said 1-bromo-4-(trifluoromethyl)benzene, about 0.055 to about 5.5 moles of said n-butyl lithium, and about 0.05 to about 5 moles of said benzaldehyde are employed.

10. The process of claim 4 wherein the temperature is about −10° C. to about 0° C.

11. The process of claim 5 wherein the residence time of step (a) is about 10 seconds to about 100 minutes, and the residence time of step (b) is about 5 seconds to about 100 minutes.

12. A process for the preparation of a compound of the formula:

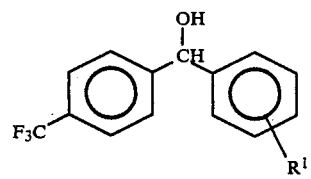

wherein R¹ is selected from the group of hydrogen, halo, halo-substituted alkyl group, halo, nitro, alkyl group, aralkyl group, cycloalkyl group, aryl group, alkaryl group, heterocyclic group containing a member selected from the group of N, O, S, or mixtures thereof, alkoxy group, aryloxy group, thioalkoxy group, and N,N-dialkyl amino which comprises:
   (a) reacting 1-bromo-4-(trifluoromethyl) benzene with n-butyl lithium in an ether solvent,
   (b) then reacting the product of step (a) with a benzaldehyde of the formula:

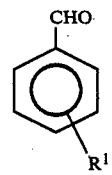

wherein R¹ has the same meaning as stated above; and
   (c) reacting the product from step (b) with an acid salt or mineral acid to thereby produce the compound of formula 1.

13. The process of claim 2 wherein said compound has the formula:

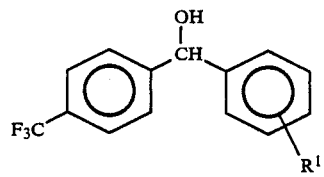

and said benzaldehyde is 4-(trifluoromethyl) benzaldehyde.

14. The process of claim 12 being carried out continuously.

15. The process of claim 14 wherein a solution of 1-bromo-4-(trifluoromethyl)benzene in an inert solvent and a solution of n-butyl lithium in an inert solvent are introduced simultaneously in a continuous manner in a tube reactor; a solution of p-(trifluoromethyl)phenyllithium is exited to a second tube reaction wherein said benzaldehyde in an inert solvent is introduced in a continuous manner.

16. The process of claim 15 wherein the inert solvent for the n-butyl lithium is a saturated aliphatic hydrocarbon and the inert solvent for the 1-bromo-4-(trifluoromethyl)benzene and for the benzaldehyde is an ether.

17. The process of claim 16 wherein said hydrocarbon is hexane and said ether is methyl-t-butyl ether.

18. The process of claim 16 about 0.05 to about 5 moles of said 1-bromo-4-(trifluoromethyl)benzene, about 0.055 to about 5.5 moles of said n-butyl lithium, and about 0.05 to about 5 moles of said benzaldehyde are employed.

19. The process of claim 12 wherein the temperature is about $-10°$ C. to about $0°$ C.

20. The process of claim 14 wherein the residence time of step (a) is about 10 seconds to about 100 minutes, and the residence time of step (b) is about 5 seconds to about 100 minutes.

21. The process of claim 12 wherein said acid salt is an aqueous solution of ammonium chloride.

22. A continuous process for preparing p-(trifluoromethyl)-phenyllithium which comprises continuously introducing 1-bromo-4-(trifluoromethyl)benzene and n-butyl lithium in the presence of inert solvent into a tube reactor.

23. The process of claim 22 wherein the inert solvent for the n-butyl lithium is a saturated aliphatic hydrocarbon and the inert solvent for the 1-bromo-4-(trifluoromethyl)benzene and for the benzaldehyde is an ether.

24. The process of claim 23 wherein said hydrocarbon is hexane and said ether is methyl-t-butyl ether.

25. The process of claim 23 about 0.05 to about 5 moles of said 1-bromo-4-(trifluoromethyl)benzene, and about 0.055 to about 5.5 moles of said n-butyl lithium are employed.

26. The process of claim 22 wherein the temperature is about $-10°$ C. to about $0°$ C.

27. The compound of claim 1 wherein $R^1$ is selected from the group of hydrogen, trihalomethyl, alkyl group having 1-8 carbon atoms, cycloalkyl group having 3-6 carbon atoms, phenyl, naphthyl, alkoxy group having 1-8 carbon atoms, phenoxy, naphthoxy, thioalkoxy having 1-8 carbon atoms, halo group, heterocyclic group containing a member selected from the group of N, O, S, or mixtures thereof; and dialkylamino group wherein said alkyl contains 1-8 carbon atoms.

28. The compound of claim 27 wherein said heterocyclic group is selected from the group of pyridine, morpholine, furan pyran and thiophene.

29. The process of claim 4 wherein $R^1$ is selected from the group of hydrogen, trihalomethyl, alkyl group having 1-8 carbon atoms, cycloalkyl group having 3-6 carbon atoms, phenyl, naphthyl, alkoxy group having 1-8 carbon atoms, phenoxy, naphthoxy, thioalkoxy having 1-8 carbon atoms, halo group, heterocyclic group containing a member selected from the group of N, O, S, or mixtures thereof; and dialkylamino group wherein said alkyl contains 1-8 carbon atoms.

30. The process of claim 29 wherein said heterocyclic group is selected from the group of pyridine, morpholine, furan, pyran and thiophene.

31. The process of claim 30 wherein the temperatures is about $-10°$ C. to about $20°$ C.

32. The process of claim 12 wherein $R^1$ is selected from the group of hydrogen, trihalomethyl, alkyl group having 1-8 carbon atoms, cycloalkyl group having 3-6 carbon atoms, phenyl, naphthyl, alkoxy group having 1-8 carbon atoms, phenoxy, naphthoxy, thioalkoxy having 1-8 carbon atoms, halo group, heterocyclic group containing a member selected from the group of N, O, S, or mixtures thereof; and dialkylamino group wherein said alkyl contains 1-8 carbon atoms.

33. The process of claim 32 wherein said heterocyclic group is selected from the group of pyridine, morpholine, furan, pyran and thiophene.

34. The process of claim 33 wherein the temperature is about $-10°$ C. to $0°$ C.

* * * * *